United States Patent [19]
Koch et al.

[11] 3,941,659
[45] Mar. 2, 1976

[54] BLOOD ALCOHOL ANALYZER

[75] Inventors: Robert B. Koch, Starkville, Miss.;
John D. Skogen, Burnsville, Minn.

[73] Assignee: Honeywell Inc., Minneapolis, Minn.

[22] Filed: July 11, 1974

[21] Appl. No.: 487,710

[52] U.S. Cl. .......................... 195/103.5 R; 195/68
[51] Int. Cl.² ...................... C12K 1/04; C07G 7/02
[58] Field of Search......... 195/103.5 R, 127, 63, 68;
23/230 B

[56] References Cited
UNITED STATES PATENTS

| | | | |
|---|---|---|---|
| 3,384,555 | 5/1968 | Guifault et al. | 195/103.5 R |
| 3,413,198 | 11/1968 | Deutsch | 195/103.5 R |
| 3,788,950 | 8/1970 | Hicks et al. | 195/103.5 R |
| 3,839,154 | 10/1974 | Messing | 195/127 |

OTHER PUBLICATIONS
R. Bonnichsen, "Ethanol" "Methods of Enzymatic Analysis" H. U. Bergmeyer, Academic Press, N.Y. & London, pp. 285-287, (1965).
Dixon et al., "Enzymes" 2nd Ed. Academic Press, N.Y. pp. 19-22, (1964).

*Primary Examiner*—A. Louis Monacell
*Assistant Examiner*—C. A. Fan
*Attorney, Agent, or Firm*—Charles G. Mersereau; Henry L. Hanson

[57] ABSTRACT

A continuous-flow method and apparatus for the determination of alcohol in a biological fluid such as blood is disclosed. A packed column containing the enzyme alcohol dehydrogenase physically entrapped in a acrylamide gel together with other special ingredients which extend the active life of the enzyme in the test environment is provided. Downstream of the packed column a transparent measurement cell is provided in conjunction with a fluorescence spectrophotometer which is utilized to measure the fluorescence of the effluent which is directly related to the amount of ethyl alcohol in the original sample. The fluorescence measurement is electrically transformed by conventional means into a direct readout of the alcohol content of the sample. This obtains from the fact that alcohol dehydrogenase catalyzes the oxidation of ethyl alcohol in the presence of non-fluorescening NAD to produce acetaldehyde and fluorescing $NADH_2$. The alcohol dehydrogenase is immobilized and its activity preserved in a manner which allows many tests to be run without any significant loss of enzyme or enzyme activity thereby accomplishing considerable cost reduction in the procedure.

5 Claims, 2 Drawing Figures

BLOOD ALCOHOL ANALYZER

BACKGROUND OF THE INVENTION

1. Field of the Invention

The present invention relates to the field of testing samples of biological fluids for specific component species and in particular, the determination of alcohol in blood by the use of fluorescence spectroscopy.

2. Description of the Prior Art

The use of enzymes in chemical analysis for the determination of various components in biological fluids is gaining rapidly as a practical analytical technique. This technique generally involves the measurement of the concentration of one or more produce species or other change in the condition of a solution following an enzyme-catalyzed reaction in which a specific enzyme is utilized to catalyze a known specific reaction. One specific reaction which has been found very useful is the detection of ethyl alcohol or other alcohols in biological fluids utilizing the enzyme alcohol dehydrogenase (ADH). It has been found that ADH catalyzes the reaction between certain alcohols, for example, ethyl alcohol and nicotinamide-adenine-dinucleotide (NAD) to produce the corresponding aldehyde plus $NADH_2$. Using ethyl alcohol as an example, the following reaction takes place:

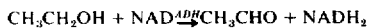

$$CH_3CH_2OH + NAD \xrightarrow{ADH} CH_3CHO + NADH_2$$

The above reaction is normally conducted with a slight excess of NAD to assure that all the ethyl alcohol is oxidized. The amount $NADH_2$ can then be measured spectrophotometrically. This has been done, for example, by measuring the $NADH_2$ at 340 nm using a conventional UV spectrophotometer.

Prior art devices utilizing the above reaction for the determination of blood alcohol concentration have been essentially batch-type operations wherein fresh enzyme must be utilized for each test. Also, special cleaning steps must be utilized to insure that residual products of one reaction are not present to interfere with readings taken for subsequent tests. The cost of continually replenishing the enzyme along with the other drawbacks associated with the batch-type operation have rendered the costs of such testing in many cases prohibitive.

SUMMARY OF THE INVENTION

According to the present invention, there is provided a method and apparatus for chemical analysis which combines an improved enzyme-catalyzed reaction system utilizing a reusable immobilized enzyme and an improved fluorometric sensing technique in a flow-through analytical system. By means of the present invention a large number of determinations may be made without replacing either the enzyme or utilizing any special cleaning procedure for the system.

Briefly, the present invention contemplates a method and apparatus for determining the concentration of an alcohol in a biological or other sample, e.g., the determination of ethyl alcohol in blood, wherein the measured sample is combined with an amount of a buffered carrier solution and introduced into a flow-through reaction chamber which may be a packed-column, for example, containing an amount of an immobilized alcohol dehydrogenase, where the desired reaction is catalyzed and takes place. After traversing the packed column, the solution, in which the desired action is substantially complete, then continues to flow, while remaining in a closed system, through a transparent cell wherein the fluorescence of the reacted solution is measured utilizing a conventional fluorescence spectrophotometer which can, by conventional electronic means, produce a recorded or other output indicating the concentration of alcohol in the sample. The effluent containing the reacted sample is then discarded via a drain.

The flow-through system of the present invention may be one utilizing a constant-head type pump or may be operated by gravity. The flowrate may be conveniently controlled by selection of size and length of the column and conduit components of the flow system such that the reaction is essentially completed by the the time the reacted solution reaches the measurement cell.

The activity of the immobilized alcohol dehydrogenase is really extended in life span and increased in amount by the provision of a specially buffered carrier solution, gelling and storage techniques. This involves the use of certain combinations of ADH stabilizers for gel preparation, storage and use. These stabilizers are normally selected from a group including ammonium sulfate (0.1 to 1.0 M), dithiothrietol (DTT) (approximately 0.001 M), glycine (approximately 1%), sodium pyrophosphate (approximately 3%), zinc cloride (approximately 0.01 M). In the carrier solution of the preferred embodiment pyrosphosphate or Tris buffer is employed in combination with ammonium solfate and DTT.

If desired, a second column-measuring cell system may be utilized wherein the packed-column does not contain any immobilized alcohol dehydrogenase but is identical to the first column in other respects. Samples may then be run through both systems and the difference in the resulting fluorescence spectrophotometer measurements utilized to derive the concentration of alcohol in the sample. This approach is most useful wherein the determination of baseline fluorescence of samples such as blood may change from sample to sample.

DESCRIPTION OF THE PREFERRED EMBODIMENT

Figure 1:
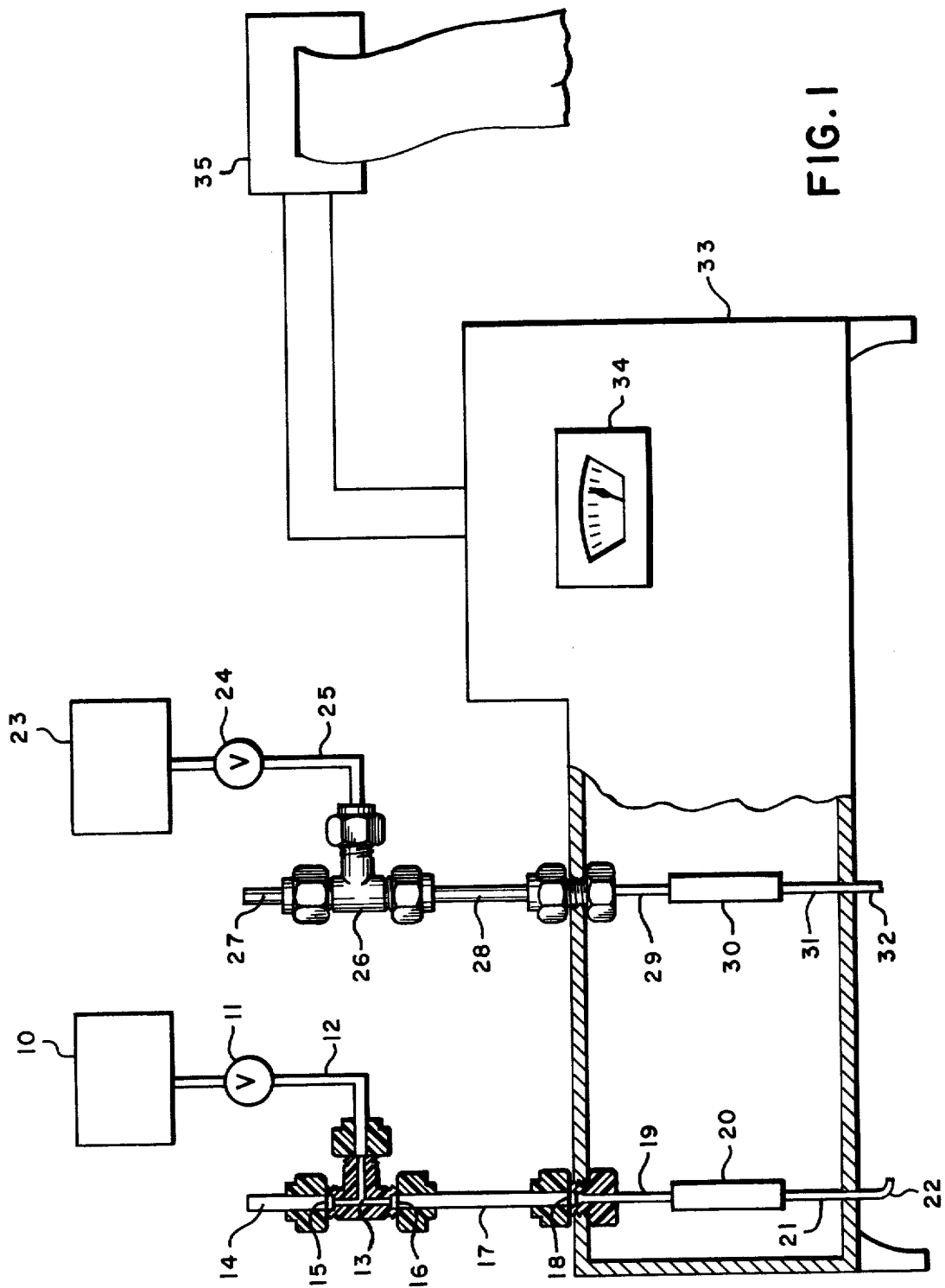
FIG. 1 is an illustration, partially in block form and partially in section, depicting the apparatus of the invention generally.

FIG. 1 depicts a typical apparatus in accordance with the present invention. For purposes of clarity some of the figure is shown in section and for simplification some conventional parts are illustrated in block form. A reservoir for containing a buffered organic carrier solution is illustrated in block form at 10. This reservoir may be in the form of a constant-head tank using a conventional overflow weir system to achieve a constant flowrate through a valve 11 and a conduit 12. The conduit 12 connects with a combining chamber 13 showing in section. A sample injection port 14 is provided for the introduction into the analytical system of the biological fluid to be analyzed. The injection may be accomplished by utilizing a graduated syringe or other premeasured, small-volume container. The bottom of the injection port 14 may be closed by a septum through which the sample is injected. In the mixing chamber 13 the carrier solution and sample solution are combined prior to analysis.

The combined solution then passes through a porous closure member 16 in which may be a fine metal screen (approximately 100 mesh) or a glass frit material of similar permeability, into a reaction column 17. The reaction column 17 contains an amount of the enzyme alcohol dehydrogenase immobilized in a finely divided cross-linked polyacrylamide gel matrix, as discussed in greater detail below. A second porous member 18, which may be identical with the member 16, closes the bottom of the column 17 in a manner which allows the test solution to defuse therethrough but prevents the loss of any of the enzyme-containing gel from the column. This solution then flows through a conduit 19 into a transparent fluorescence-measurement cell 20. After the fluorescence is measured in a manner discussed in greated detail below, the measured effluent solution then flows through a final conduit 21 to a drain opening as at 22 where it is discarded.

If samples of the biological fluid to be analyzed have a background fluorescence which may vary from sample to sample, as is the case with whole blood samples, a second or reference flow system may be provided substantially identical to the first system with one noteable exception. Thus, the second system, not shown in section, has a constant head supply 23 which supplies solution through a valve 24 via a conduit 25 to a mixing chamber 26 associated with a sample injection port 27. The combined solution then flows through a column 28, conduit 29, fluorescence-measurement cell 30 and a conduit 31 to a drain 32. A septum similar to 15 and semipermeable or diffusion membranes similar to 16 and 18 are also provided in this second system although not illustrated. The only difference between the two systems is the fact that the gel located in the reaction column 28 contains no immobilized enzyme corresponding to that contained in the reaction column 17.

Remaining system components include a fluorescence spectrophotometer shown partially in section at 33 which may be equipped with a readout meter 34 and a recording output device as at 35.

The several conduit means and chambers connected thereby in both the analysis and reference systems may be made of glass tubing or any other conventional material normally used for such analytical apparatus. The one important limitation, of course, is that they must be constructed of a material which does not chemically affect or is not affected by the solutions passing therethrough. The connecting fittings also may be any conventional type fittings compatable with the materials used in constructing the conduit and chambers. Thus, screwed compression fittings have been used, for example.

The gel utilized for entrapping the enzyme is a specially prepared crossed-linked acrylamide gel in which cross-linking agent is normally N, N'-methylenebisacrylamide and wherein the mole ratio of the acrylamide monomer to the cross-linking agent is normally in the range from about 45:1 to about 55:1 and the solids content is about 21 percent. The high ratio gel used yields a much improved enzyme lattice in which leaching out of ADH molecules is greatly reduced. The general preparation of the gel is well known in the art and that of a particularly successful gel is more fully described in the copending application of Koch et al., Ser. No. 425,043 filed Dec. 14, 1973 (which is a division of Ser. No. 276,630 filed July 31, 1972, now abandoned) and assigned to the same assignee as the present application.

An important aspect of the present invention in regard to the immobilization and longer-term use of the ADH lies in the particular technique of keeping the ADH activity at a high level for a relatively long period of time. It has been found that ADH, in contrast to many other successfully immobilized enzymes, required chemical stabilizers in gelling, storage and use in order to keep its activity at a sufficiently high level for more than a few hours. The stabilizers which have been effectively used include ammonium sulfate (0.1 M to 1.0 M) dithiothrietol (DTT) — (approximately 0.001 M), glycine (approximately 1%), sodium pyrophosphate (approximately 3%), and zinc chloride (approximately 0.01 M).

Tests on supernatant and gel activity showed that the above stabilizers indeed keep the ADH from inactivating during the gelling process. Experimentation to date indicates that use of all of the above stabilizers during gelling produces the most active immobilized ADH.

After successful preparation of active immobilized ADH was achieved, much experimentation was required to determine the best method of retaining this activity both in storage of the immobilized ADH and its use in the analytical column environment.

Some of the more important results of the experimental work in varying the preparation and storage conditions for the immobilized ADH are shown in tables I-A and I-B, below.

TABLE I

COMPARATIVE ACTIVITY[a] OF TWO GELS UNDER DIFFERECT STORAGE CONDITIONS

I-A Same Gels Tested In Column Repeatedly

| Days | Gel I Solution | | | Gel II Solution | | |
|---|---|---|---|---|---|---|
| | A | B | C | A | B | C |
| 2 | | | 99.3 | | | 124.6 |
| 3 | | | 79.5 | | | 97.4 |
| 6 | | | 82.5 | | | 77.4 |
| 7 | | | 88.0 | | | 84.9 |
| 8 | 14.8 | | | 0 | | |
| 9 | | 71.3 | | | 69.9 | |
| 10 | | 49.4 | | | | |
| 13 | | 32.7 | | | 21.8 | |
| 14 | | | 68.8 | | | 69.6 |
| 42 | | | 11.3 | | | 9.5 |

I-B Stored Gel Portions Previously Unused

| Days | Gel I Solution | | | Gel II Solution | | |
|---|---|---|---|---|---|---|
| | A | B | C | A | B | C |
| 2 | | | 99.3 | | | 124.6 |
| 8 | 14.8 | | | 0 | | |
| 9 | | 71.3 | | | 69.9 | |
| 10 | 11.5 | | | | | |
| 15 | | | 95.3 | | | 114.8 |
| 28 | | | 54.7 | | | |
| 35 | | 75.0 | | | 109.0 | |
| 36 | 1.0 | | | 0 | | |
| 44 | | 58.5 | | | | |
| 48 | | | | | | 119.2 |

Conditions: Gel I prepared with all stabilizers[b] including 1.0 M $(NH_4)_2SO_4$.
Gel II prepared with all stabilizers including 0.1 M $(NH_4)_2SO_4$.
Each gel was divided into three equal portions (A,B,C) and soaked in 10 ml of different solutions as follows:

Solution A: 0.1 M Phosphate Buffer, pH 7.4 $(NH_4)_2SO_4$ gel conc.), $10^{-3}$M DTT.

Solution B: $(NH_4)_2SO_4$ (gel conc.), $10^{-3}$M DTT.

TABLE I-continued

COMPARATIVE ACTIVITY[(1)] OF TWO GELS
UNDER DIFFERECT STORAGE CONDITIONS
I-A Same Gels Tested In Column Repeatedly

| Days | Gel I Solution | | | Gel II Solution | | |
|---|---|---|---|---|---|---|
| | A | B | C | A | B | C |

Solution C: $(NH_4)_2SO_4$ (gel conc.), $10^{-3}$M DTT - then dried in $N_2$ Stream with hydration prior to tests.

[(1)] Activity values are expressed in % and correspond to an arbitrary $NADH_2$ reference concentration of 0.14, μM set at 100%. This is an accurate gage of the ability of the enzyme to catalyze the $ETOH + NAD \rightarrow CH_3CHO + NADH_2$ reaction.
[(2)] Ammonium sulfate (0.1 N to 1.0 M, dethiothrietol (DTT)-(approximately 0.001), glycine (approximately 1%), sodium pyrosphosphate (approximately 3%), and zinc chloride (approximately 0.01 M).

Table I shows experimental results of two gels which were prepared to determine optimum storage conditions, optimum concentration of $(NH_4)_2SO_4$, and gel longevity.

Table I-A shows activity of the same gel column on different days. Between testing, gels were returned to the indicated (i.e., A, B or C) storage conditions. The results obtained from corresponding portions of Gels I and II are similar indicating no significant difference due to the indicated levels of $(NH_4)_2SO_4$ concentration used in gel formation. However, the gels soaked in the presence of 0.1 M phosphate (A portions) even initially had very low or no enzyme activity, indicating phosphate buffer should not be used to store the gel. The gels soaked in $(NH_4)_2SO_4$ and DTT (B portions) had more activity than those in the A portion. However, the gel activity did drop substantially with time over a period of only 3 days. The gels soaked in $(NH_4)_2SO_4$ and DTT, which were dried for storage and rehydrated for each test (C portions) maintained activity quite well over a period of about 2 weeks.

Table I shows comparative activity of samples of the gel from a previously unused (i.e., stored unused since preparation) portion I-B of the same gel prep used in Table I-A. Table I-B shows the same general trend for corresponding portions of Gels I and II. The buffer soaked gels (A portions) were very low in activity. Those soaked without buffer (B portions) were again higher in activity than the A portions but still lower than the C portions which were dried for storage and rehydrated just before testing. This again shows that drying the gel is the best method of storage. Since portion C of Gel II was consistently higher in activity than portion C of Gel I it appears that gels should be prepared with 0.1 M $(NH_4)_2SO_4$ rather than the 1.0 M solution.

The buffer utilized in the carrier solution may be any one which does not interfere with the desired analytical reaction and does not in itself fluoresce or inhibit the activity of the ADH during its useful life in the column. The most desirable range of pH in which the desired reaction should be conducted is from about 7.5 to about 8.5. Although other buffer systems no doubt can be used, success has been achieved using a buffer solution of 0.02 M to 0.04 M sodium pyrophosphate or about 0.1 M Tris (hydroxymethyl) aminomethane buffer.

In the buffered carrier solution and analytical environment described, it has been found that reproducibility of results over an 8 hour period have been good. Because of the decreases in gel activity from day to day, however, the gel should be calibrated each day by running a standard aqueous alcohol solution to recalibrate the system.

As mentioned above, the amount of $NADH_2$ which is directly related to the amount of alcohol in a given sample can be measured either spectrophotometrically or flurospectrophotomatrically. The level of lethal dosage of alcohol in human blood is approximately 0.5% and the range of concentrations for legal intoxication is from approximately 0.05% to approximately 0.15%, depending on the applicable state law, of course. At very low concentrations of $NADH_2$ fluorescence spectroscopy can be many times more sensitive than regular spectroscopy. Thus, the fluorescent method of $NADH_2$ measurement is preferred, since in the determination of ethyl alcohol concentration found in a sample of blood, the range of 0 to 0.5% is all that is required to be measured. In this range tests results have indicated that approximately one hundred times the sensitivity of regular spectroscopy may be achieved by utilizing fluorescence spectroscopy in the system of the present invention.

As indicated above, because of the variation in background fluorescence of samples of whole or blood serum, it is normally necessary to compare a blank or unreacted sample with a reacted sample to determine the amount of fluorescence attributable solely to the production of $NADH_2$. As shown in FIG. 1, and described above, this is best achieved by utilizing a second or reference column of like dimensions packed with a gel of the same composition as the first column but containing no enzyme. By comparing the difference in fluorescence between blank sample and the measured sample the amount of fluorescence directly attributable to the ADH action on alcohol may be determined.

In one experimental embodiment, sample and reference columns were prepared by utilizing glass columns approximately 2.5 inches long by 0.13 inches I.D. The sample column was filled with ADH gel wherein the concentration of ADH in the gel was approximately 2 mg (900 units) per ml of gel and wherein the gel was screened through a number 20 sieve. The reference columns were attached to cells downstream of the columns in which the fluorescence could be measured. A flow of buffer solution consisting of aqueous solution of 0.032 M (pH 7.9) sodium pyrophosphate buffer, 0.038 M ammonium sulfate, and 0.001 M DTT was established at a rate of approximately 0.764 ml/min. The constant flow rate was obtained by utilizing a Harvard infusion pump equipped with 50 ml syringes. Identical samples of whole blood containing NAD in the approximate concentration of 0.0035 M and, measuring approximately 50 μl were injected into flowing solution. After the solution containing the samples had traversed the analysis and reference columns, samples of the effluent were collected and the amount of fluorescence measured for each. The size of the columns was such that the reaction in the column containing the enzyme was substantially completed by the time the effluent emerged from the bottom of that column. A Perkin-Elmer-Hitachi flurorescence spectrophotometer (model MPF-2A) equipped with a recorder output was utilized to record the fluorescence both the analysis and reference samples. With that instrument a reading of 100% is set to equal 0.14 μM $NADH_2$.

Figure 2:
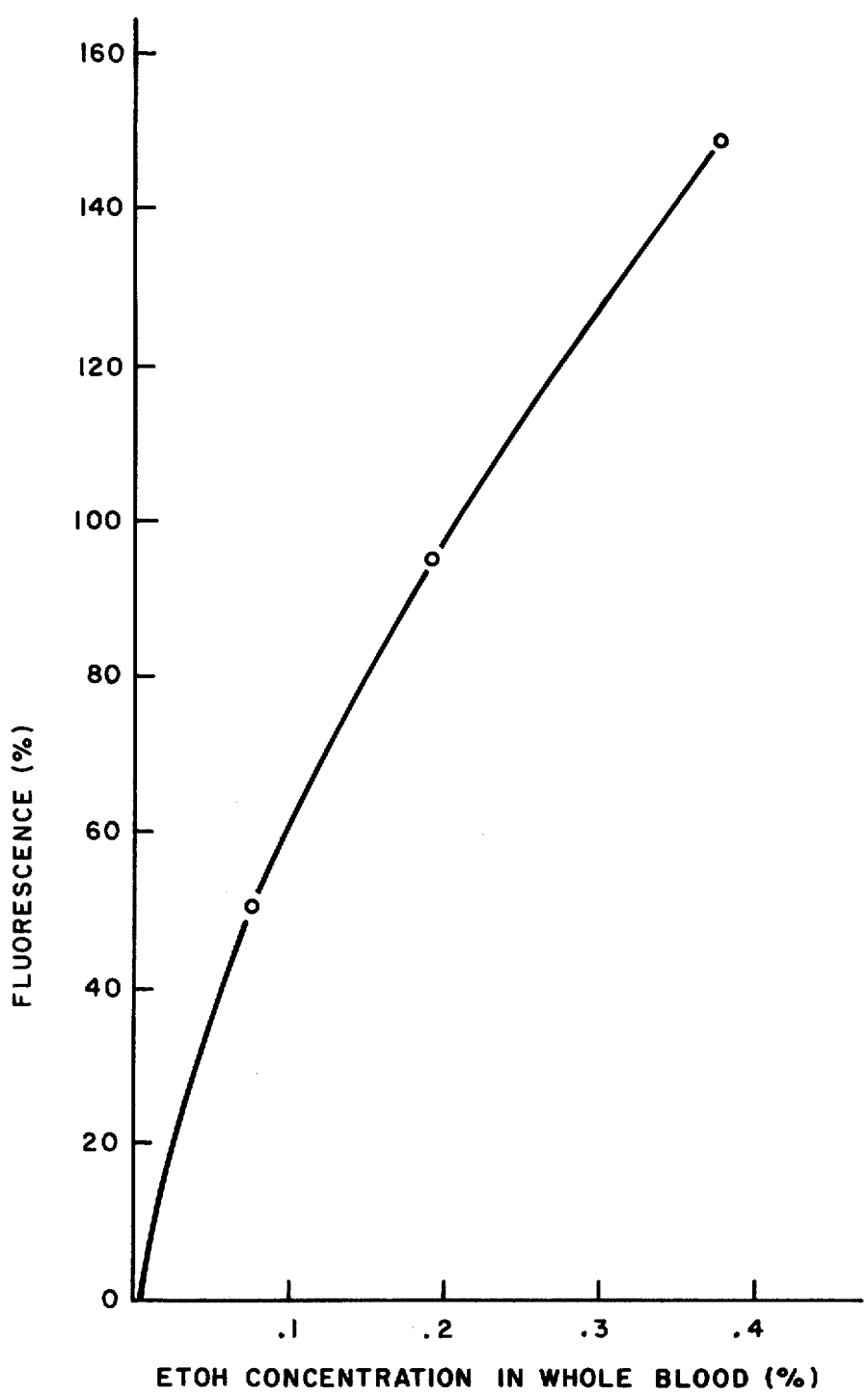
FIG. 2 is a graphical illustration depicting the relationship between the fluorescence of the effluent and the percentage of alcohol in a blood sample.

A graph depicting the amount of fluorescence, i.e., the fluorescence obtained in the analysis equal to the difference between the analysis and reference fluorescence reading is depicted in FIG. 2. It is known that NAD when converted to NADH$_2$ by the ADH column has a fluorescence excitation peak of approximately 346 nm and an emission peak at approximately 457 nm. Thus, the fluorescence spectrophotometer utilized is normally set on these peaks and, in the experimentation described above, a 4 nm slit or bank width was used in the excitation spectrum and a 16 nm slit or band was utilized in the emission spectrum.

One problem that has been encountered in the analysis of the ethyl alcohol concentration found in whole blood samples occurs because of red blood cell interference which may greatly reduce the corresponding fluorescence reading. However, it has been found that red blood cells travel through the system at a much faster rate than the fluorescencing product of the enzyme reaction and therefore it is possible to obtain excellent blood alcohol concentration values by reading the fluorescence value of the effluent after substantially all the red blood cells have passed by, i.e., by reading the last one-third of the effluent, for example.

Although the preferred embodiment is described with particular reference to the detection of ethyl alcohol, alcohol dehydrogenase has been found useful in detecting a broad range of compounds including primary, secondary and tertiary alcohols, glycerol, cyclopentanol, cyclohexanol, amino-ethanol, steriods, etc. Of importance, is the fact that none of the above compounds (which could cause interference in blood alcohol determination) are normally present in blood at a concentration that would interfere with blood alcohol measurements.

It should also be noted that inasmuch as the rate of the enzyme-catalyzed reaction involved is somewhat temperature dependent, conventional temperature control means may be required in applications where temperature variations are likely.

The embodiments of the invention in which an exclusive property or right is claimed are defined as follows:

1. In a method of determining the concentration of an alcohol of interest in a sample wherein the detection of the concentration or change therein of the indicating species NADH$_2$ produced by the reaction of said alcohol with NAD in a buffered carrier solution in the presence of the enzyme ADH wherein said ADH is immobilized by physical entrapment in a cross-linked polyacrylamide gel in a manner which allows free contact between the species in the buffered carrier solution and the enzyme molecules with little or no loss of enzyme into said carrier solution thereby and wherein after said reaction is substantially complete, the reacted solution is caused to fluoresce, said fluorescence is measured and an output indicative of said fluorescence is generated, the improvement comprising the step of adding a quantity of one or more stabilizers selected from the group consisting of:

Ammonium Sulfate (0.1 M to 1.0 M)
   Dithiothrietol (approximately 0.001 M)
   Glycine (approximately 1%)
   Sodium Pyrophosphate (approximately 3%)
   Zinc Chloride (approximately 0.01 M)

and during the gelling of said gel.

2. A method of claim 1 including the steps of placing said immobilized enzyme in a packed column and controlling the flowrate of said buffered carrier solution through said column.

3. The method of claim 1 wherein said alcohol is ethyl alcohol and said sample is a solution of blood.

4. The method of claim 1 wherein all of said stabilizers are added and wherein the concentration of said ammonium sulfate added is approximately 0.1 M.

5. The method of claim 1 including the further steps of soaking said prepared gel in an aqueous solution of approximately 0.1 M ammonium sulfate and approximately 0.001 M dithiothrietol and drying said gel in a stream of gaseous nitrogen prior to storage.

* * * * *